United States Patent [19]

Corbeil

[11] 4,144,136

[45] Mar. 13, 1979

[54] APPARATUS FOR CELLULAR CULTURE

[75] Inventor: Michel Corbeil, Laval-des-Rapides, Canada

[73] Assignee: Institut Armand-Frappier, Canada

[21] Appl. No.: 804,075

[22] Filed: Jun. 6, 1977

[51] Int. Cl.² .............................................. C12K 9/00
[52] U.S. Cl. .................................... 195/127; 195/142; 195/1.8
[58] Field of Search ........................ 195/127, 142, 143

[56] References Cited

U.S. PATENT DOCUMENTS

| 3,711,379 | 1/1973 | Adams | 195/127 |
| 3,732,149 | 5/1973 | Santero | 195/127 |
| 3,827,943 | 8/1974 | Mann | 195/127 |
| 3,853,712 | 12/1974 | House | 195/127 |

Primary Examiner—Alvin E. Tanenholtz
Attorney, Agent, or Firm—Seidel, Gonda & Goldhammer

[57] ABSTRACT

There is described a method of cellular culture wherein a suspension of anchorage dependent cells is provided, the suspension is introduced in at least one culture vessel containing tubes disposed parallel and at a constant distance to one another, the culture vessel is rotated in such a manner and at a speed effective to cause adhesion of the cells on the inner wall of said culture vessel and on the inner and outer walls of the tubes and an aerobic condition is created in said culture vessel. The apparatus is also described.

14 Claims, 2 Drawing Figures

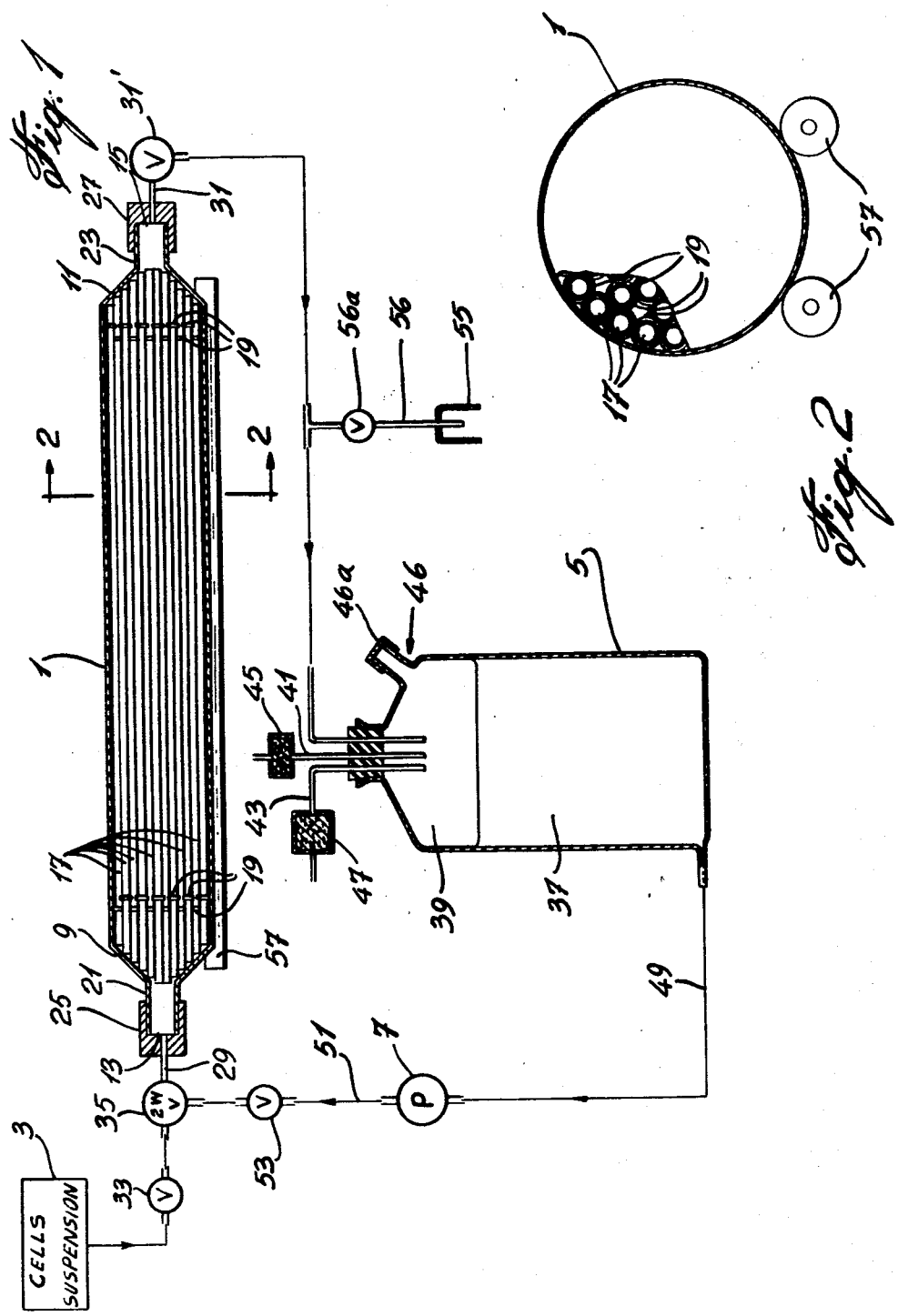

APPARATUS FOR CELLULAR CULTURE

This invention relates to a method and an apparatus for cellular culture. More particularly, the invention relates to the production of cells by a method which enables much improved yields to be obtained within a culture vessel.

Mainly, cellular cultures of animal origin are derived from chicken embryos, human tissues, monkey tissues and the like. It is also known that there is a need for massive cellular culture because of the increasing activity in virology, cell biology and cancer research. Also, it is desirable to substantially improve the present methods of production of cellular culture.

It is well known that the cultivation of cells is performed by first preparing by dispersion of an organ, a cell supension, in a suitable medium. The suspension is then introduced in a culture vessel in which the cells sediment and adhere to the wall of the vessel when they multiply. As a result of multiplication which takes place in a few days, a monolayer of cells is obtained. Simultaneously or subsequently these cells can be used "in situ" for virus propagation or can be harvested, diluted and used for seeding other vessels or used for various purposes.

Presently, the cultivation of cells is performed in flat bottom flasks such as the Blake bottle, the Roux flask and plastic flasks which allow growth of the anchored cells on one surface only. It is also performed in rolling bottles where the entire inner wall of the bottle serves for anchorage and growth of the cells. Systems have been developed in which a number of rolling bottles or tubes are assembled and serviced altogether by means of manifolds (Santero, U.S. Pat. No. 3,732,149; Mann, U.S. Pat. No. 3,827,943).

Another known system is based on increasing the surface by the addition of plates. The plates are made of glass or titanium and can rotate about an axis. These culture units are very expensive to construct and have a great number of moving parts which make them very delicate. In view of the fact that cells have a normal tendency to descend vertically in their suspension, these plates must be mounted horizontally. Thus, in order to obtain adhesion of the cells on both surfaces of the plates, the unit must be rotated intermittently 180°, for several hours resulting in a back and forth movement of the substrate in relation to the sedimenting cells. As a consequence of such manipulations, uniform distribution of the cells on the surfaces of the plates is not obtained. Moreover, proper microscopic examination of the cell sheet is not possible.

Other methods and apparatuses for culturing cells are also known such as exemplified by the following U.S. Patents: U.S. Pat. No. 3,821,087, June 28, 1974, Knazek et al; U.S. Pat. No. 3,873,423, Mar. 25, 1975, Munder et al; U.S. Pat. No. 3,948,732, Apr. 6, 1976, Haddad et al; U.S. Pat. No. 3,997,396, Dec. 14, 1976, Delente.

However, it will be realized that all of these methods and apparatuses are either too complicated or are unsatisfactory.

In order to overcome the disadvantages of the prior art and to substantially improve cellular culture, there is provided a method of cellular culture which comprises:

(a) providing a suspension of anchorage dependent cells;

(b) introducing this suspension of cells in one culture vessel containing tubes disposed parallel to and at a constant distance from one another;

(c) rotating the culture vessel in such a manner and at a speed effective to cause adhesion of the cells on the inner wall of the culture vessel and on the inner and outer walls of the tubes; and (d) creating an aerobic condition in the culture vessel.

In order to carry on this method there is provided an apparatus which comprises:

(a) at least one culture vessel;

(b) tubes disposed inside the culture vessel parallel to and at a constant distance from one another;

(c) means to introduce a suspension of cells in the culture vessel;

(d) means creating an aerobic condition in the culture vessel; and (e) means to cause a rotation of the culture vessel and of the tubes about an axis parallel to the tubes.

Depending on the needs, the suspension of cells is prepared from tissue of animal, vegetal or protist origin, and in a suitable culture medium.

When cells of animal origin are selected, they are preferably selected from primary cultures, non permanent diploid cell lines, and permanent cell lines.

The manner used for introducing the cells into the culture vessel can be selected at will and it can vary a great deal. However, the suspension of cells can be poured manually into the culture vessel, it can be introduced by gravity flow from a separate reservoir containing this suspension of cells or it can also be pumped into the culture vessel from a separate reservoir which contains the suspension of cells.

The so filled vessel is closed at both ends and rotated about an axis on a mechanically operated rolling device. The rolling phase in the culture process, which is performed for a few hours only, is to allow adhesion of the cells on all available which are passing continuously for several hours, under the descending cells. As a result, a uniform distribution of the cells on the substrate is obtained.

In accordance with a preferred embodiment according to the invention, there is provided a separate supply of liquid medium, which is in contact with a gaseous phase, and this separate supply of liquid medium is circulated through the culture vessel at a rate sufficient to bring nutrients and dissolved gases necessary for cellular growth, with the proviso that the rate of circulating does not cause shearing of the cells from the walls of the culture vessel or of the tubes mounted inside the culture vessel.

The liquid medium can be monitored in order to adjust the pH and the pressure of dissolved gases.

Although the rate of circulation of the liquid medium through the culture vessel can vary to a certain extent provided there is no shearing of the cells from the walls of the vessel and of the tubes, it has been found out that better results will be obtained by adjusting the rate of circulation of the liquid medium at about 0.5 to about 1.5 ml of liquid medium per minute per 100 $cm^2$ of growth surface.

The amount of suspension of cells which is introduced into the culture vessel should preferably be sufficient to submerge all the tubes which are mounted in the culture vessel in order to permit cell growth on all surfaces available within the culture vessel.

The invention will now be illustrated by means of the annexed drawings which are given only for the purpose of illustration, and in which FIG. 1 is a flow diagram of an apparatus including a culture vessel according to the invention adapted to carry out cellular culture; and FIG. 2 is a partial cross-section taken along line 2—2 of FIG. 1.

Referring to the drawings, it will be seen that the device according to the invention essentially consists of a culture vessel 1, a liquid supply 3 to contain a suspension of cells, a container 5 for the culture medium and a pump 7.

As shown in FIGS. 1 and 2, the culture vessel 1, which is preferable made of Pyrex (trade mark) borosilicate glass but which can also be made of an inert plastic allowing anchorage of the cells, is elongated and cylindrical. The culture vessel 1 is formed with tapered ends 9 and 11 and both tapered ends 9, 11 are provided with respective openings 13, 15. It will be realized that opening 13 will serve to introduce the cells suspension or the culture medium into the container 1 while the opening 15 will be used for the removal of the cell suspensions or the liquid medium from the culture vessel 1.

Inside the culture vessel 1 there are a plurality of small tubes 17 which, as shown, are spaced and parallel to one another. The length of the tubes inside the culture vessel is not too critical. However, it will be obvious that better yield would be obtained by providing tubes which will occupy as much as the length of the culture vessel as possible. For example, the tubes 17 could, as shown in FIG. 1, occupy substantially the entire interior space of the culture vessel. Of course, it may be easier for mounting the tubes inside the apparatus to make them of the same length, such as to just clear the tapered ends 9 and 11.

The tubes 17 should be at equal distance to one another. For this purpose, a small spacer 19 is mounted near the end of each tube and the distribution of these spacers 19 could be as shown in FIG. 1 or in any other arrangement provided they do not touch one another. It has been found preferable to use tubes in which the inner diameter is about 7 mm and the outer diameter is about 9 mm. The spacer 19 should be such as to provide for the closest distance between each tube to be about 1 mm.

These spacers 19 should be made of inert material in order to have no reaction with the cells and the culture medium.

It was mentioned above that the culture vessel should be made of PYREX or of an inert plastic which would allow anchorage of the cells. The same is true with respect with the tubes 19. In practice, PYREX is used because it is more easy to work with and it is resistant to sterilization temperature and has good optical properties.

Each of the tapered ends 9, 11 is terminated by a tubular portion 21, 23 formed with the respective openings 13, 15. The tubular portions 21 and 23 are closed by special types of stoppers 25, 27 enabling rotation of the culture vessel while the stoppers 25, 27 remain fixed. Stopper 25 is connected to a duct 29 for introducing the cell suspension or the culture medium into the culture vessel 1. Stopper 27 is the same as stopper 25 except that it is mounted over tubular portion 23 and is connected to duct 31 which will be used to remove the culture medium or cell suspension from the culture vessel 1.

As mentioned above, the cell suspension is contained in a supply container 3. The suspension is introduced into the culture vessel by means of duct 29 along which there is mounted a stopper valve 33 and a two-way valve 35 the purposes of which will be discussed later when the operation of the device will be described.

Duct 31 is used to recirculate the culture medium from the culture vessel 1 into the reservoir 5. In order to create an aerobic condition inside the culture vessel 1, the culture medium 37 which is allowed to circulate through the culture vessel 1 is in contact with air 39. This is made possible by providing air inlets 41 and 43 each of which is adapted with a respective filter 45, 47 to make sure that no undesirable impurity is introduced into the culture vessel 1. Also, a side arm 46 provided with a screwed cap 46a is welded on the reservoir 5 for sampling, withdrawal or introduction purposes. As mentioned above, circulation of the culture medium is made possible by the use of a peristaltic pump 7 which withdraws the culture medium from reservoir 5 through duct 49 and forces the latter along duct 51, through stopper valve 53, two-valve 35 and a portion of duct 29.

In order to determine the amount of cells which is still to be deposited on the walls of the culture vessel 1 and the inner and outer walls of the tubes 19, there is provided a sampling device 55 which is connected to duct 31 by means of a duct 56 along which there is a stopper valve 56a.

Finally since the culture vessel 1 must be rotated, it is mounted on motorised rollers 57 which will cause rotation of the vessel at any desired speed.

In operation, the first step consists in introducing a suspension of cells from container 3 through duct 29 by opening stopper valve 33 and allowing valve 35 to block off any circulation from duct 51. As soon as the culture vessel 1 is filled i.e. when the tubes are submerged with the cells suspension, stopper 33 is closed, and so are both valves 35 and 31'. After a rotation period on rollers 57, valve 31' is opened, the valve 35 is adjusted to connect duct 29 with duct 51, the stopper valve 53 is opened and the pump is put into operation to enable a circulation of the culture medium through the culture vessel 1 in order to make sure that the nutrients are vehiculed and an aerobic condition is maintained in said cultured vessel 1. At the onset of media circulation the rolling operation is ceased.

Of course, the invention has been illustrated by means of one (1) single culture vessel. It is obvious that a plurality of culture vessels could be used whether they be in series or in parallel. An operation could also be set up by having a plurality of culture vessels hooked up to independent circuits to produce three (3) types of culture cells at the same time.

In the examples which follow the experiments were made using arrangements of one culture vessel or a plurality set in series.

The following experiments were performed as described.

Cell culture was performed with the VERO cell line and with a human ambryonic lung diploid line (IMH-P). Both cell lines were propagated in a media composed of a mixture of equal parts of 199-Hanks base amd MEM-Earle's base, completed with 10% fetal bovine serum.

For adhesion, the culture vessels are filled with the cell suspension and closed with standard screw caps and rotated for a period of 4 hours at a speed of 10 rph on a Rollacell apparatus (New Brunswick model). The culture vessels of 4.5 and 5.5 cm diameter are rotated. After cell attachment, the culture vessels are set for media circulation by screwing the modified caps aleady attached to the tubing leading to the media reservoir, in replacement of the standard caps, after which the media is circulated by the peristaltic pump. The cell growth is monitored by examination with an inverted microscope. Results are summarized in the table.

For cell harvesting, the standard caps are screwed at each end, from this point the culture vessels are manipulated as a roller bottle.

The media is discarded and the proper volume of trypsin is poured in. The trypsin is shaken in the culture vessel and immediately discarded. Fresh trypsin is put back, shaken and the culture vessel is allowed to rotate 10 minutes on the roller apparatus. A volume of serum free media is added to the culture vessel. After shaking the culture vessel, the cell suspension is poured out and counted.

For sampling purposes, a sampling device is introduced in the unit circuit.

Technical Data on Culture Vessel Modules and Corresponding Media Reservoirs, Volume and Circulation

| DATA | MODULES | | | |
|---|---|---|---|---|
| | Culture Vessel 1 | Culture Vessel 4 | Culture Vessel 8 | Culture Vessel 16 |
| Bottles : diameter | 4.5 cm | 5.5 cm | 5.5 cm | 11 cm |
| length | 15 cm | 29 cm | 58 cm | 40 cm |
| wall surface | 212 cm$^2$ | 518 cm$^2$ | 1036 cm$^2$ | 1382 cm$^2$ |
| *Glass tubing : number | 15 | 25 | 25 | 76 |
| total surface | 1125 cm$^2$ | 3780 cm$^2$ | 7250 cm$^2$ | 15200 cm$^2$ |
| Total growth surface | 1337 cm$^2$ | 4268 cm$^2$ | 8286 cm$^2$ | 16582 cm$^2$ |
| Growth surface increase factor of original bottle | 6.3 X | 8.2 X | 8.2 X | 12.6 X |
| Media volume capacity | 250 ml | 750 ml | 1500 ml | 3000 ml |
| Preferred total media volume** | 650 cc | 2000 cc | 4000 cc | 8000 cc |
| Media reservoir capacity (surface available for gas exchange) | 1 l (80 cm$^2$) | 2 l (115 cm$^2$) | 4 l (175 cm$^2$) | 8 (300 cm$^2$) |
| Working media volume in reservoir | 400 cc | 1250 cc | 2500 cc | 5000 cc |
| Preferred rate range of media** circulation (ml/unit) | 5–10 | 20–40 | 50–100 | 100–200 |
| Recommended volume of trypsin used for harvesting | 35–50 ml | 100 ml | 200 ml | 400 ml |

*Prior to first washing cycle
**For single culture vessel arrangement

GROWTH RESULTS WITH VERO AND IMH-P (7 DAY CULTURES)

| | | NB. CELLS SEEDED/CM$^2$ | $\overline{X}$ NB. CELLS HARVESTED/CM$^2$ |
|---|---|---|---|
| VERO | culture vessel 1 | 1.8 × 10$^4$ | 1.5 × 10$^5$* |
| | culture vessel 8 | 1.8 × 10$^4$ | 3.0 × 10$^5$ |
| | roller bottle | 1.5 × 10$^4$ | 1.1 × 10$^5$* |
| IMH-P | culture vessel 1 | 5.2 × 10$^4$ | $\overline{X}$ 2.8 × 10$^5$ |
| | culture vessel 4 | 5.2 × 10$^4$ | $\overline{X}$ 2.5 × 10$^5$ |
| | culture vessel 8 | 5.2 × 10$^4$ | $\overline{X}$ 2.4 × 10$^5$ |
| | culture vessel 16 | 3.07 × 10$^4$ | 2.4 × 10$^5$ |
| | roller bottle | 5.2 × 10$^4$ | 2.1 × 10$^5$ |

N.B.: In all experiments, a 4 hour period was allowed for adhesion at a rotating speed of ± 10 RPH. Media is changed after 3–4 days of culture.
*No media change.

I claim:

1. Apparatus for effecting cellular culture which comprises:
   (a) at least one culture vessel;
   (b) a plurality of discrete tubes having an opening at each end thereof disposed inside said culture vessel parallel and equi-distant to one another;
   (c) means to introduce a suspension of cells in said culture vessel;
   (d) means creating an aerobic condition in said culture vessel; and
   (e) means to cause rotation of said culture vessel and of said tubes about an axis parallel to the longitudinal axis of said tubes.

2. Apparatus according to claim 1 wherein said culture vessel is elongated and cylindrical.

3. Apparatus according to claim 2 wherein said culture vessel is tapered at both ends, each of said ends being formed with an opening adapted to introduce or remove liquid from said culture vessel.

4. Apparatus according to claim 3, wherein the length of said tubes in said culture vessel varies depending on the space which is available in said culture vessel.

5. Apparatus according to claim 4, wherein the inner diameter of each said tube is about 5 to 7 mm and the outer diameter of said tube is about 7 to 9 mm.

6. Apparatus according to claim 5, wherein the closest distance between each of said tubes is about 1 mm.

7. Apparatus according to claim 5, wherein said closest distance is obtained by mounting inert rings around said tubes.

8. Apparatus according to claim 7, which comprises means to proportion the total volume inside the tubes and the total volume outside the tubes respectively to the total surfaces inside the tubes and the total surfaces outside the tubes.

9. Apparatus according to claim 1, wherein said culture vessel and said tubes are made of borosilicate glass.

10. Apparatus according to claim 1, wherein said culture vessel and said tubes are made of inert plastic allowing anchorage of said cells.

11. Apparatus according to claim 1 further comprising a reservoir to contain a liquid medium in contact with a gaseous phase within said reservoir, duct means connecting said culture vessel and said reservoir, and a pump associated with said duct means enabling said liquid medium to circulate through said duct means and said culture vessel.

12. Apparatus according to claim 2 wherein said means to cause rotation comprises motorized rollers bearing against said culture vessel.

13. Apparatus according to claim 1 wherein said tubes occupy substantially the entire interior space of said culture vessel.

14. Apparatus for effecting cellular culture comprising at least one elongated cylindrical culture vessel having at least one end tapered toward an opening at that end of the culture vessel, a plurality of discrete tubes having an opening at each end thereof occupying substantially the entire interior space of said culture vessel, said tubes being located parallel to each other and parallel to the major wall of said culture vessel, said tubes being spaced from said major wall and being spaced from each other at an equal distance by inert spacing means, means to introduce a suspension of cells into said culture vessel through an opening at an end of said culture vessel, means creating an aerobic condition within said culture vessel, and means for rotating said culture vessel and tubes about an axis parallel to the longitudinal axis of said tubes.

* * * * *